United States Patent
Agarwal

(10) Patent No.: US 9,968,377 B2
(45) Date of Patent: May 15, 2018

(54) SPINAL RODS FORMED FROM POLYMER AND HYBRID MATERIALS AND GROWTH ROD DISTRACTION SYSTEM INCLUDING SAME

(71) Applicant: Anand K. Agarwal, Holland, OH (US)

(72) Inventor: Anand K. Agarwal, Holland, OH (US)

(73) Assignee: Spinal Balance, Inc., Toledo, OH (US)

( * ) Notice: Subject to any disclaimer, the term of this patent is extended or adjusted under 35 U.S.C. 154(b) by 0 days. days.

(21) Appl. No.: 14/776,046

(22) PCT Filed: Mar. 17, 2014

(86) PCT No.: PCT/US2014/030241
§ 371 (c)(1),
(2) Date: Sep. 14, 2015

(87) PCT Pub. No.: WO2014/145470
PCT Pub. Date: Sep. 18, 2014

(65) Prior Publication Data
US 2016/0022316 A1    Jan. 28, 2016

Related U.S. Application Data

(60) Provisional application No. 61/790,117, filed on Mar. 15, 2013.

(51) Int. Cl.
*A61B 17/88* (2006.01)
*A61B 17/70* (2006.01)
*A61L 31/06* (2006.01)

(52) U.S. Cl.
CPC .......... *A61B 17/70* (2013.01); *A61B 17/7002* (2013.01); *A61B 17/705* (2013.01);
(Continued)

(58) Field of Classification Search
CPC ............ A61B 17/7002; A61B 17/7053; A61B 2017/681; A61B 17/7041; A61B 17/7076;
(Continued)

(56) References Cited

U.S. PATENT DOCUMENTS 5,700,263 A * 12/1997 Schendel ............. A61B 17/663
606/57
7,029,472 B1 * 4/2006 Fortin ................ A61B 17/7047
606/105
(Continued)

FOREIGN PATENT DOCUMENTS

FR    2900563 A1    11/2007

OTHER PUBLICATIONS

Extended European Search Report, Application No. EP14764274.8 dated Nov. 10, 2016.

*Primary Examiner* — Eduardo C Robert
*Assistant Examiner* — Tara R Carter
(74) *Attorney, Agent, or Firm* — MacMillan, Sobanski & Todd, LLC

(57) ABSTRACT

A growth rod distraction system a domino having first and second bores provided therein. First and second spinal rods are respectively disposed within the first and second bores for movement relative to the domino. First and second spur gears are disposed within the domino and respectively cooperate with the first and second growth rods such that rotation of the spur gears causes axial movements of the growth rods relative to the domino. The spinal rods may be formed either from a flexible polymer material (such as a PEEK, carbon fiber PEEK, PEAK, or similar medical grade polymer material) or a hybrid combination of such flexible polymer material and a metallic material (such as nitinol or similar medical grade metallic material). The spinal rods can
(Continued)

also be used for fusion or non-fusion surgery of the spine to stabilize two or more vertebrae.

18 Claims, 7 Drawing Sheets

(52) U.S. Cl.
CPC ...... *A61B 17/7014* (2013.01); *A61B 17/7016* (2013.01); *A61B 17/7031* (2013.01); *A61L 31/06* (2013.01); *A61B 2560/04* (2013.01); *A61L 2430/38* (2013.01)

(58) Field of Classification Search
CPC .............. A61B 17/7011; A61B 17/705; A61B 17/7001; A61B 17/7077
USPC .................................................. 606/250–279
See application file for complete search history.

(56) References Cited

U.S. PATENT DOCUMENTS

| | | | |
|---|---|---|---|
| 2006/0195088 A1 | 8/2006 | Sadler et al. | |
| 2008/0300633 A1* | 12/2008 | Jackson | A61B 17/702 606/257 |
| 2009/0012565 A1* | 1/2009 | Sachs | A61B 17/7041 606/246 |
| 2009/0093820 A1* | 4/2009 | Trieu | A61B 17/7004 606/103 |
| 2009/0192514 A1 | 7/2009 | Feinberg et al. | |
| 2009/0240284 A1* | 9/2009 | Randol | A61B 17/7004 606/254 |
| 2010/0100133 A1* | 4/2010 | Carl | A61B 17/7053 606/279 |
| 2011/0301643 A1* | 12/2011 | Jahng | A61B 17/3421 606/254 |
| 2012/0101527 A1 | 4/2012 | Conner | |
| 2012/0283781 A1 | 11/2012 | Amin | |

* cited by examiner

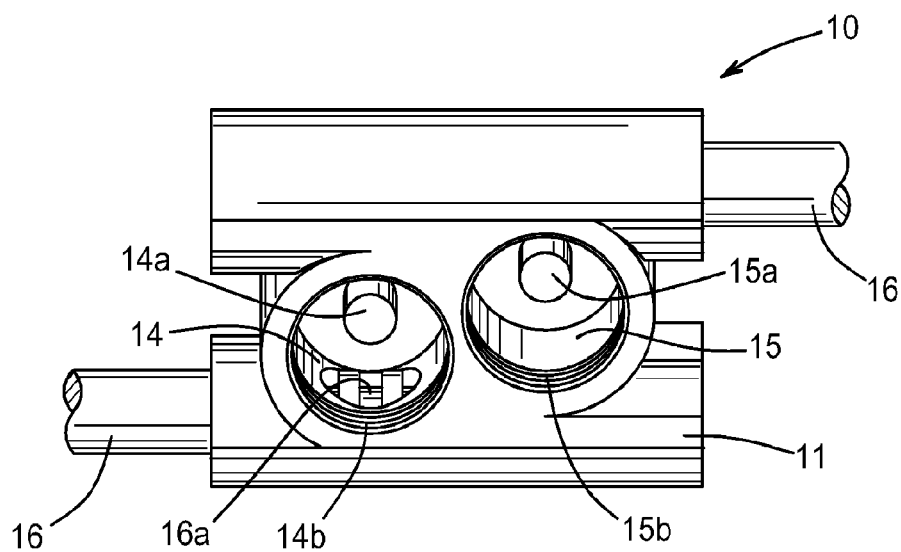
FIG. 4
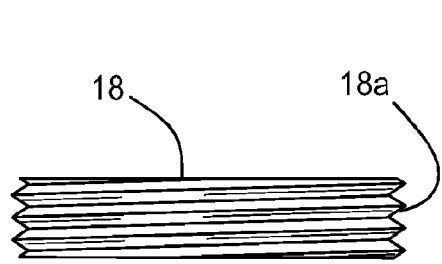
FIG. 5
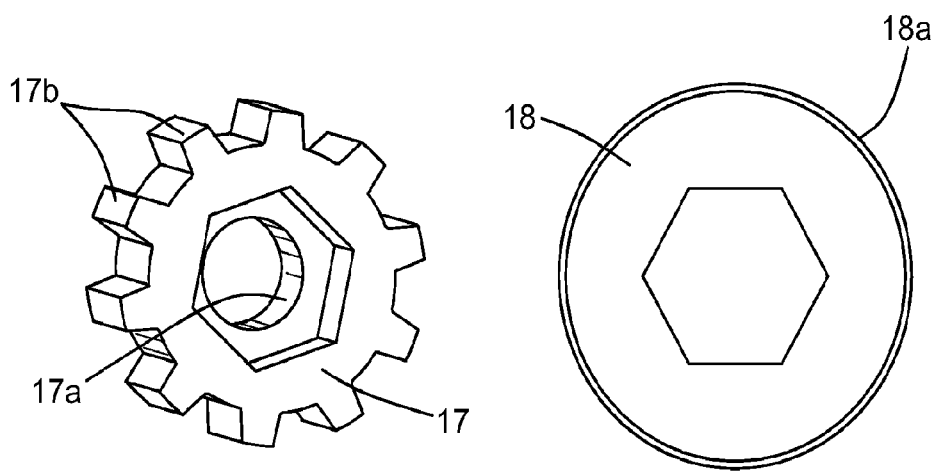
FIG. 6
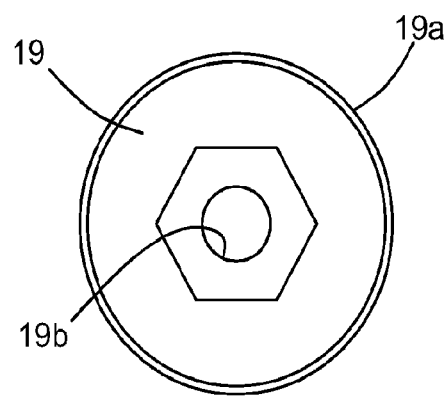
FIG. 7
FIG. 8

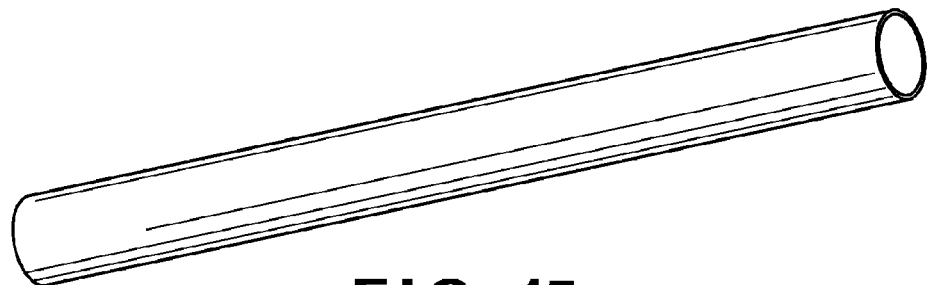
F I G. 15
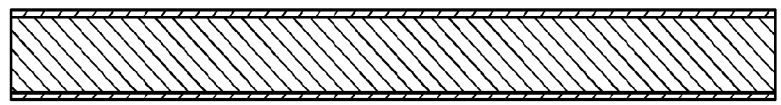
F I G. 16
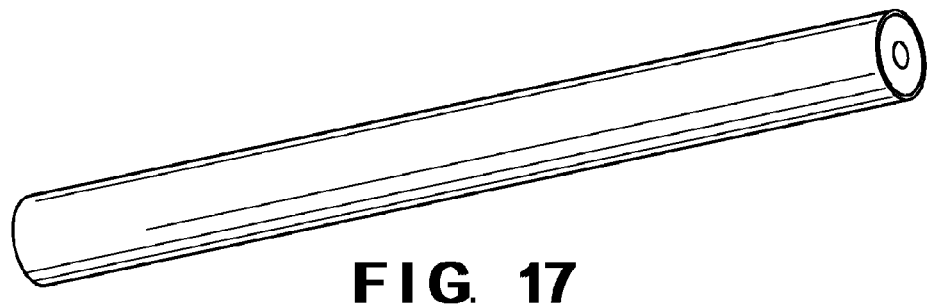
F I G. 17
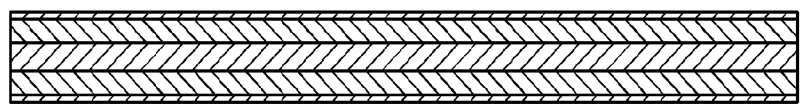
F I G. 18

SPINAL RODS FORMED FROM POLYMER AND HYBRID MATERIALS AND GROWTH ROD DISTRACTION SYSTEM INCLUDING SAME

CROSS-REFERENCE TO RELATED APPLICATIONS

This application claims the benefit of U.S. Provisional Application No. 61/790,117, filed Mar. 15, 2013, the disclosure of which is incorporated herein by reference.

BACKGROUND OF THE INVENTION

This invention relates to the field of orthopedic implants, more specifically, a polymer PEEK (polyether ether ketone), carbon fiber PEEK, PEAK or hybrid (polymer and metal) based spinal rods which are used for deformity corrections with growth preservation in early-onset scoliotic patients and for the fusion of two or more vertebrae in degenerative spinal disease or deformity. This invention also relates to a mechanism for the minimally invasive distraction of such a rod.

Surgical techniques for the treatment of early-onset scoliosis are aimed at deformity correction with preservation of growth. The most common approach includes the use of distraction-based growth rods. A typical growth rod fixation has two foundations, namely, proximal and distal, where limited fusion is performed. Pedicle screws, hooks, wires, and other retaining structures may be used at each foundation to anchor the rods with the bony structure. Each foundation has a rod spanning toward the other end, which are connected to each other near the thoracolumbar junction. The rods are connected using a domino, which helps in distraction for serial surgeries until a final fusion is performed.

In a single growth rod technique, the rods span only one side (the concave side) of the spinal deformity curve. In a dual growth rod technique, the rods span both (both the concave and convex sides) of the spinal deformity curve. For the dual growth rod technique, the region of the rod near the foundation can have a crosslink connecting the rods of both sides.

In a typical growing rod implant surgery, the rods are attached along one or both sides of the spine above and below the spinal deformity curve using the pedicle screws or other retaining structures. The rod is then extended to correct the spinal deformity curve until the surgeon feels enough compression in the rod to stop the adjustment. The spinal deformity curve can usually be corrected by fifty percent at the time of the initial surgery. During the first operation, the patient usually undergoes invasive surgery. Regular construct lengthening is typically scheduled approximately every six months to a year thereafter. The lengthening procedure usually includes exposing the domino connectors through a small midline incision, loosening either the cranial or the caudal domino-connector setscrews, and distracting across the two rods within the connector. This lengthening process is frequently continued for a period of five to ten years after implantation.

Although known spinal and growth rod structures and installation procedures have functioned satisfactorily, several potential limitations have been determined. First, current spinal rods are made out of metallic materials, such as stainless steel, cobalt-chromium, or titanium. As a result, these metal spinal and growth rods are very rigid. The high level of rigidity of these metal spinal and rods may restrict the micro-motion of intervertebral disc in the spine, which can cause spontaneous fusion at the intervertebral junction. Spontaneous fusion is an undesirable clinical complication because the aim of the growth rod surgery is to delay or limit spinal fusion so as to allow the spine to grow. Second, current spinal rods are known to experience a relatively high rate of breakage. The material used to form the rod is an important consideration because it is a construct bearing load for a longer duration without spinal fusion, and its durability is vital. Third, the current surgical technique exposes the patient to a chance of infection because of the midline exposure of the tissue during subsequent distraction surgeries. Even though the use of minimally invasive techniques may reduce the chance of infection, none of the current mechanical distraction systems are simple enough for distraction, and some have many sub-units. Therefore, it would be desirable to avoid all of these potential problems.

SUMMARY OF THE INVENTION

This invention relates to a flexible growth rod system that militates against spontaneous fusion at the intervertebral junction, and which also militates against adjacent level degeneration polymer such as PEEK, PEAK, and other medical grade polymer or hybrid (both metal and polymer) rod, which would provide better deformation during physiologic loads and will reduce the incidence of rod breakage due to higher demand for flexibility is innovated. Further the rod has novel minimal invasive mechanisms attachments which would avoid big open reoperations to distract the rod during regular intervals, thereby preventing pain, infection, and morbidity of patients.

This invention includes a polymer, where a preferred embodiment is one of PEEK, PEAK, carbon fiber PEEK, and other medical grade polymers or hybrid (polymer and metal) spinal rods.

Polymer (such as PEEK, PEAK, or other medical grade polymers) or hybrid (such as PEEK, PEAK, or carbon fiber with a nitinol core) spinal rods could be made for use in any growth rod technique and with any generic instruments, such as pedicle screws, hooks, dominoes, etc). The hybrid rod can be of two types, namely: (1) a composite rod with hollow outer cylinder made of nitinol and inner rod of the polymer (such as PEEK, PEAK, carbon fiber, or any other medical grade polymer), wherein the outer metal may have serrations to increase the flexibility, or (2) a composite rod with hollow outer cylinder (having a circular, oval, or other desired cross sectional shape) made of polymer (such as PEEK, PEAK, carbon fiber, or any other medical grade polymer) and inner rod of the nitinol.

Minimally invasive distractible growth rods could be assembled using a compact domino that connects and houses the two ends of the rods at the thoracolumbar junction. The mechanism incorporated within the compact domino may include two spur gears, each for the distraction mechanism of proximal and distal rods. The rod region within the domino may have a special rack-like surface that uses the rotary motion of the spur gear to translate the rod along its central axis. The rod could be made out of metal or polymer or composite materials. The spur gear may be connected to the domino such that it allows the rotation of the gear. Two screw heads can be used as closings to secure and compress the spur gears inside the domino. The compression of the spur gears with the screw head closings retracts the rotation of the gears. Since the spur gears and the associated rods have dependent motion, the rods also stay fixed due to compression on the spur gears. The domino, screw head closings, and the spur gears may be made out of any desired material or materials including, for example, metals such as titanium or stainless steel.

An in-series distractible growth rod can alternatively be made using a screw mechanism in which the two rods (proximal and distal) extend within a coupler. The coupler can be rotated using a bevel gear on the top and housed inside a domino. The coupler and bevel gear will be in a compact domino. The rotation of the coupler will push the two rods by virtue of a screw mechanism, thereby causing distraction. This mechanism could operated by a microelectric motor with a microcircuit that is activated by a remote control.

Various aspects of this invention will become apparent to those skilled in the art from the following detailed description of the preferred embodiments, when read in light of the accompanying drawings.

BRIEF DESCRIPTION OF THE DRAWINGS

FIG. 4 is a sectional elevational view of the first embodiment of the growth rod distraction system illustrated in FIGS. 1, 2, and 3.

FIG. 5 is an enlarged perspective view of one of the screw heads for the first embodiment of the growth rod distraction system illustrated in FIGS. 1 through 4.

FIG. 6 is side elevational view of the screw head illustrated in FIG. 5.

FIG. 7 is an enlarged perspective view of one of the spur gears for the first embodiment of the growth rod distraction system illustrated in FIGS. 1 through 4.

FIG. 8 is an enlarged perspective view of an alternative structure for one of the screw heads for the first embodiment of the growth rod distraction system illustrated in FIGS. 1 through 4.

FIG. 15 is a perspective view of a third embodiment of a spinal rod that can be used in any of the embodiments of the growth rod distraction system or for any other spinal surgery for fusion or non-fusion technique in accordance with this invention.

FIG. 16 is a sectional elevational view of the third embodiment of the spinal rod illustrated in FIG. 15.

FIG. 17 is a perspective view of a fourth embodiment of a spinal rod that can be used in any of the embodiments of the growth rod distraction system or for any other spinal surgery for fusion or non-fusion technique in accordance with this invention.

FIG. 18 is a sectional elevational view of the fourth embodiment of the spinal rod illustrated in FIG. 17.

DETAILED DESCRIPTION OF THE PREFERRED EMBODIMENT

Figure 1:
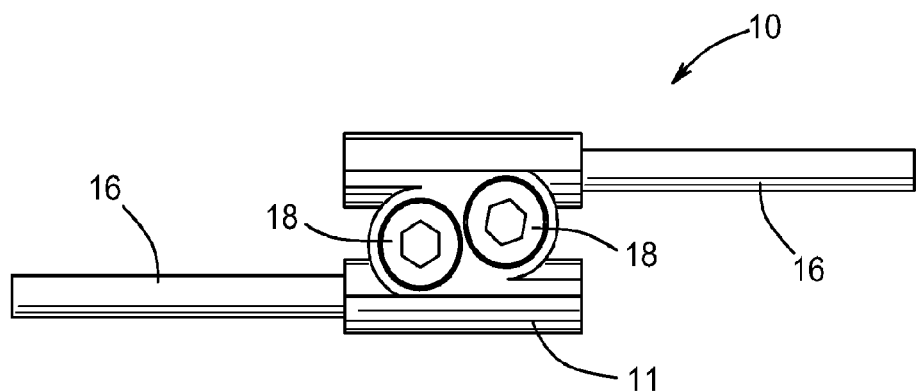
FIG. 1 is an elevational view of a first embodiment of a growth rod distraction system in accordance with this invention.
Figure 2:
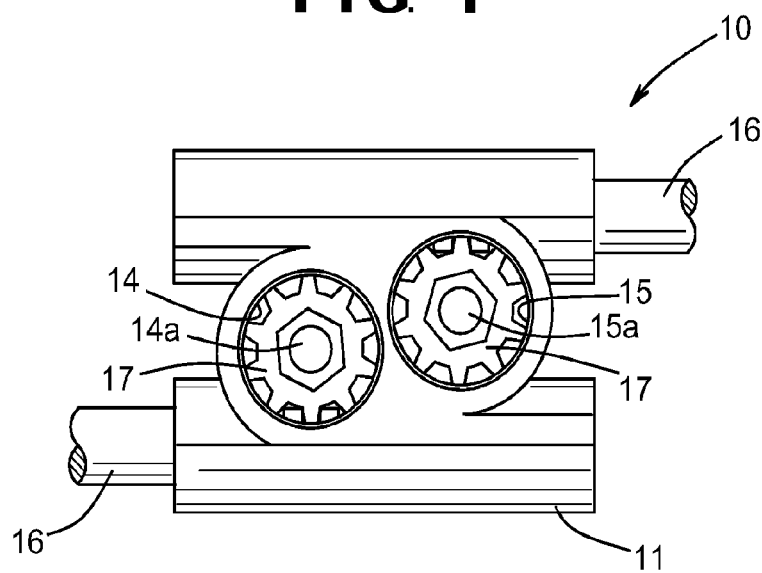
FIG. 2 is an enlarged elevational view of the first embodiment of the growth rod distraction system illustrated in FIG. 1 with the screw heads removed.
Figure 3:
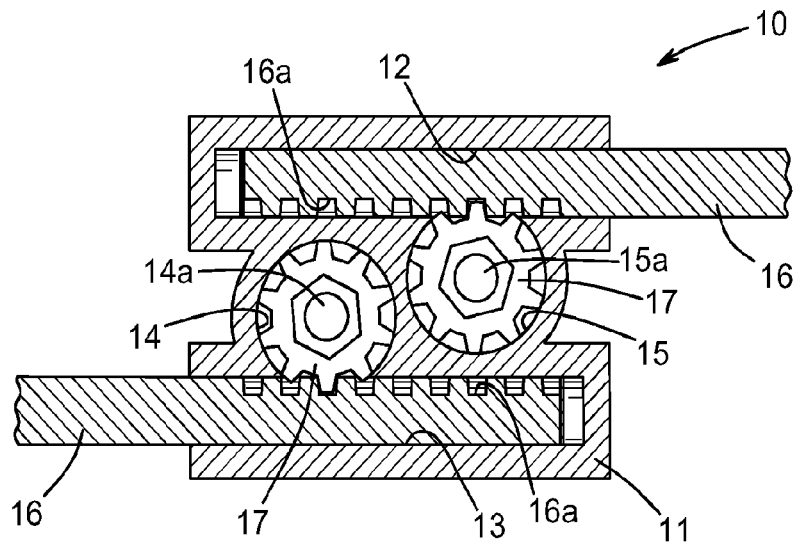
FIG. 3 is a perspective view of the first embodiment of the growth rod distraction system illustrated in FIG. 2 with the spur gears removed.

Referring now to the drawings, there is illustrated in FIGS. 1 through 4 a first embodiment of a compact, minimally invasive, and distractible growth rod distraction system, indicated generally at 10, in accordance with this invention. The growth rod distraction system 10 includes a central domino or housing 11. In the illustrated embodiment, the domino 11 includes first and second side portions having respective first and second bores 12 and 13 provided therein. Each of the illustrated first and second bores 12 and 13 is generally hollow and cylindrical in shape, having an opened end and a closed end. The illustrated bores 12 and 13 extend generally parallel to one another. However, it will be appreciated that the first and second bores 12 and 13 may have any desired shape or combination of shapes and may be oriented in any desired relationship. In the illustrated embodiment, the domino 11 also includes a central portion that extends between the first and second side portions and that has first and second openings 14 and 15 provided therein. The illustrated first and second openings 14 and 15 are each generally hollow and cylindrical in shape and, as shown in FIGS. 2 through 4, extend respectively through the domino 11 into the first and second bores 12 and 13. Respective posts 14a and 15a are provided within the first and second openings 14 and 15 for a purpose that will be explained below. The outer ends of the first and second openings 14 and 15 are threaded, as shown at 14b and 15b in FIG. 4, again for a purpose that will be explained below.

First and second growth rods 16 are respectively disposed within the first and second bores 12 and 13 of the domino 11, as shown in FIGS. 1 through 4. The structures of the growth rods 16 are illustrated in detail in FIG. 5. As shown therein, the illustrated growth rods 16 are each generally cylindrical in shape, preferably corresponding with the shapes of the first and second bores 12 and 13 within which they are respective supported. For example, the growth rods can each define outer diameters of 4.5 mm, 5.5 mm, or 6.35 mm depending upon the particular application. However, it will be appreciated that the growth rods 16 may have any desired shape or combination of shapes. Inner ends of the growth rods 16 are supported within the first and second bores 12 and 13 of the domino 11 for axial movement relative thereto, as will be explained in detail below. The outer surfaces of the inner ends of the growth rods 16 are provided with respective pluralities of recesses 16a, the purpose of which will also be explained below. The material or group of materials used to form the growth rods 16 will discussed further below.

First and second spur gears 17 are respectively disposed within the first and second openings 14 and 15 of the domino 11, as shown in FIGS. 2 and 3. The structure of one of the spur gears 17 is illustrated in detail in FIG. 5. As shown therein, the illustrated spur gear 17 has a central opening 17a and a plurality of outer teeth 17b. The central opening 17a is adapted to receive one of the posts 14a and 15a therein so as to allow each of the spur gears 17 to be disposed within the first and second openings 14 and 15. When so disposed, the spur gears 17 are supported for rotation relative to the domino 11. Also, some of the outer teeth 17b of the spur gears 17 extend into engagement with some of the recesses 16a provided in the growth rods 16. As a result, rotation of the spur gears 17 causes axial movement of the associated growth rods 16 relative to the domino 11. The purpose for this cooperation between the spur gears 17 and the growth rods 16 will be explained below.

The spur gears 17 can be retained within the respective openings 14 and 15 of the domino 11 and locked in position relative thereto by respective heads 18, as shown in FIG. 1. The structure of one of the heads 18 is illustrated in detail in FIGS. 6 and 7. As shown therein, the illustrated head 18 is shaped generally in the form of a flat disc, having an outer circumferential surface 18a that is threaded. The threaded outer circumferential surfaces 18a of the heads 18 are sized and shaped to cooperate with the threaded outer ends 14b and 15b of the first and second openings 14 and 15, as shown in FIG. 1, so as to retain the spur gears 17 within the first and second openings 14 and 15 of the domino 11. Further rotation of the heads 18 cause them to frictionally engage the associated spur gears 17, thereby preventing the spur gears 17 from to rotating within their respective openings 14 and 15. This prevents axial movement of the growth rods 16 relative to the domino 11.

In use, the heads 18 of the growth rod distraction system 10 are initially loosened or removed so as to not engage the respective spur gears 17. As a result, the spur gears 17 are free to rotate within their respective openings, allowing free axial movement of the growth rods 16 relative to the domino 11. The outer ends (not shown) of the growth rods 16 are then anchored to respective bony structures by means of pedicle screws, hooks, wires, or other conventional retaining structures (not shown) as described above. These anchors form the proximal and distal foundations for the growth rod distraction system 10 by attaching the outer ends of the growth rods 16 to the bony structure of spine. After the desired distraction of the bony structure of spine has been achieved by the surgeon, the heads 18 are installed and/or tightened on the domino 11. As discussed above, the heads 18 are caused to frictionally engage the associated spur gears 17, thereby preventing the spur gears 17 from to rotating within their respective openings 14 and 15, and further preventing axial movement of the growth rods 16 relative to the domino 11.

FIG. 8 illustrates an alternative structure for one of the screw heads 19 for the first embodiment of the growth rod distraction system illustrated in FIGS. 1 and 6. The alternative head 19 is shaped generally in the form of a flat disc, having an outer circumferential surface 19a that is threaded. The threaded outer circumferential surfaces 19a of the heads 19 are sized and shaped to cooperate with the threaded outer ends 14b and 15b of the first and second openings 14 and 15, as shown in FIG. 1, so as to retain the spur gears 17 within the first and second openings 14 and 15 of the domino 11. Additionally, however, the alternative head 19 has an aperture 19b provided therein that is sized and shaped to receive one of the posts 15a therein when the head 19 is secured to the domino 11.

Figure 9:
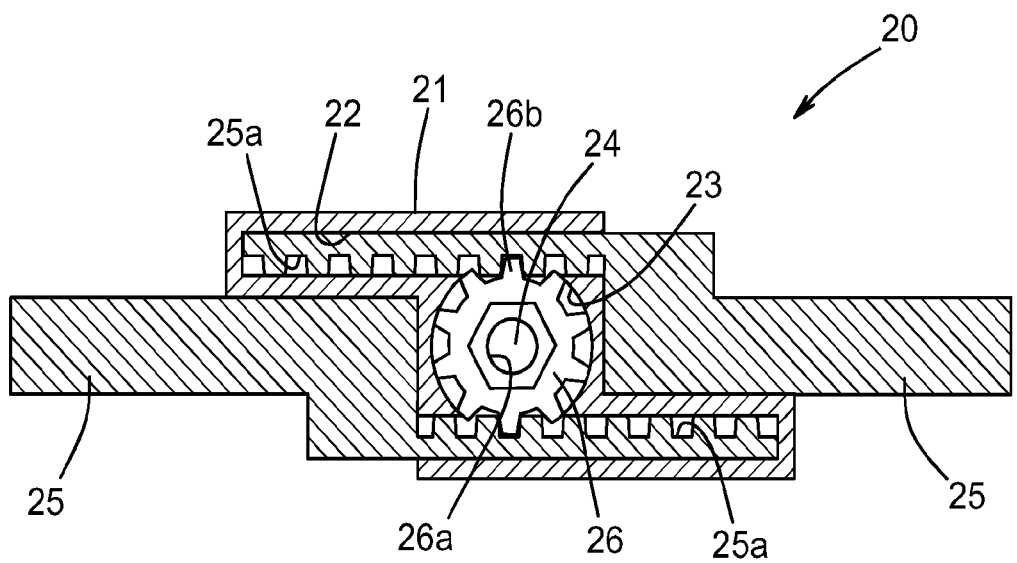
FIG. 9 is a sectional elevational view of a second embodiment of a growth rod distraction system in accordance with this invention.

FIG. 9 illustrates a portion of a second embodiment of a growth rod distraction system, indicated generally at 20, in accordance with this invention. The growth rod distraction system 20 includes a central domino or housing 21 having a single bore 22 provided therein. In the illustrated embodiment, the domino 21 also includes a single opening 23 having a post 24 provided therein. The outer end of the openings 23 threaded in the same manner as the openings 14 and 15 described above.

First and second growth rods 25 have respective inner ends that are supported within the bore 22 of the domino 11 for axial movement relative thereto, as will be explained in detail below. The outer surfaces of the inner ends of the growth rods 25 are provided with respective pluralities of recesses 25a for the same purpose as described above. The material or group of materials used to form the growth rods 25 will discussed further below.

A single spur gear 26 is disposed within the opening 23 of the domino 21 and includes a central opening 26a and a plurality of outer teeth 26b. The central opening 26a is adapted to receive the post 24 therein so as to allow the spur gear 26 to be disposed within the opening 23 for rotation relative to the domino 21. Also, some of the outer teeth 26b of the spur gear 26 extend into engagement with some of the recesses 25a provided in both of the growth rods 25. As a result, rotation of the spur gear 26 causes concurrent axial movement of both of the growth rods 25 relative to the domino 21. The spur gear 26 can be retained within opening 23 of the domino 21 and locked in position relative thereto by a head (not shown) in the same manner as described above. The operation of the second embodiment of the growth rod distraction system 20 is otherwise similar to the operation of the first embodiment of the growth rod distraction system 10 described above.

Figure 10:
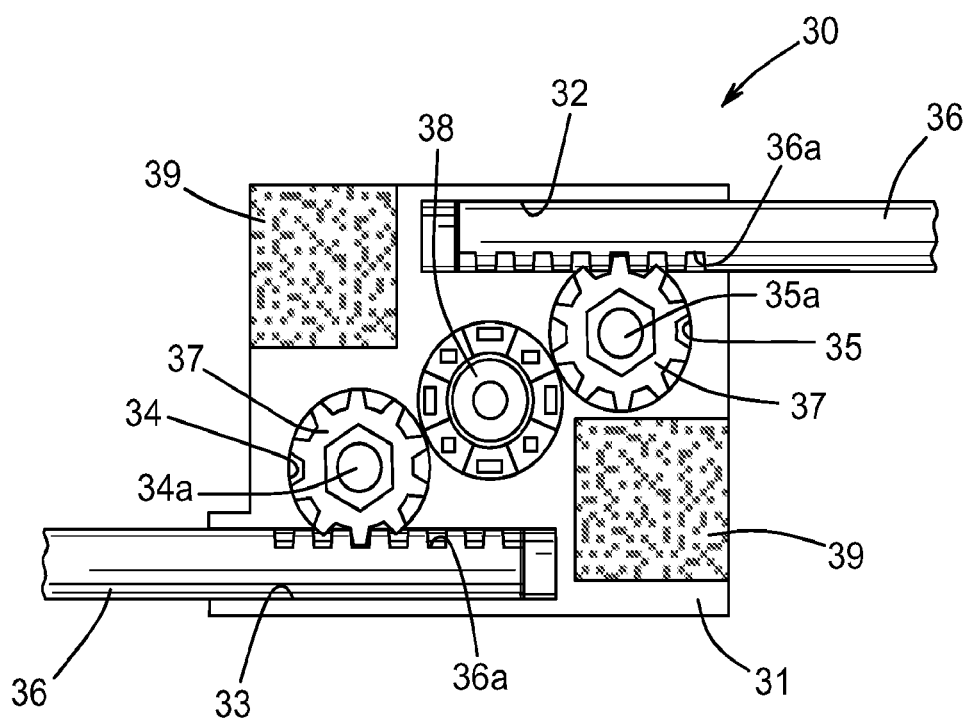
FIG. 10 is a sectional elevational view of a third embodiment of a growth rod distraction system in accordance with this invention.

FIG. 10 illustrates a portion of a third embodiment of a growth rod distraction system, indicated generally at 30, in accordance with this invention. The growth rod distraction system 30 includes a central domino or housing 31. In the illustrated embodiment, the domino 31 includes first and second side portions having respective first and second bores 32 and 33 provided therein. Each of the illustrated first and second bores 32 and 33 is generally hollow and cylindrical in shape, having an opened end and a closed end. The illustrated bores 32 and 33 extend generally parallel to one another. However, it will be appreciated that the first and second bores 32 and 33 may have any desired shape or combination of shapes and may be oriented in any desired relationship. In the illustrated embodiment, the domino 31 also includes a central portion that extends between the first and second side portions and that has first and second openings 34 and 35 provided therein. The illustrated first and second openings 34 and 35 are each generally hollow and cylindrical in shape and extend respectively through the domino 31 into the first and second bores 32 and 33. Respective posts 34a and 35a are provided within the first and second openings 34 and 35. The outer ends of the first and second openings 34 and 35 are threaded as described above.

First and second growth rods 36 are respectively disposed within the first and second bores 32 and 33 of the domino 31. The illustrated growth rods 36 are each generally cylindrical in shape, preferably corresponding with the shapes of the first and second bores 32 and 33 within which they are respective supported. However, it will be appreciated that the growth rods 36 may have any desired shape or combination of shapes. Inner ends of the growth rods 36 are supported within the first and second bores 32 and 33 of the domino 31 for axial movement relative thereto. The outer surfaces of the inner ends of the growth rods 36 are provided with respective pluralities of recesses 36a. The material or group of materials used to form the growth rods 36 will discussed further below.

First and second spur gears 37 are respectively disposed within the first and second openings 34 and 35 of the domino 31. Each of the spur gears 37 has a central opening 37a and a plurality of outer teeth 37b. The central opening 37a is adapted to receive one of the posts 34a and 35a therein so as to allow each of the spur gears 37 to be disposed within the first and second openings 34 and 35. When so disposed, the spur gears 37 are supported for rotation relative to the domino 31. Also, some of the outer teeth 37b of the spur gears 37 extend into engagement with some of the recesses 36a provided in the growth rods 36. As a result, rotation of the spur gears 37 causes axial movement of the associated growth rods 36 relative to the domino 31.

In this embodiment of the invention, a micro-motor 38 or other actuator mechanism is supported within the domino 31 of the growth rod distraction system 30. The micro-motor 38 is, of itself, conventional in the art and may be controlled by an external remote control structure (not shown) by means of one or more micro-circuits 39 that are also supported within the domino 31. The micro-motor 38 includes a rotor that engages each of the spur gears 37. Thus, when the micro-motor 38 is actuated, the rotor is rotated, thereby causing concurrent rotation of the spur gears 37. The operation of the third embodiment of the growth rod distraction system 30 is otherwise similar to the operation of the first embodiment of the growth rod distraction system 10 described above.

Figure 11:
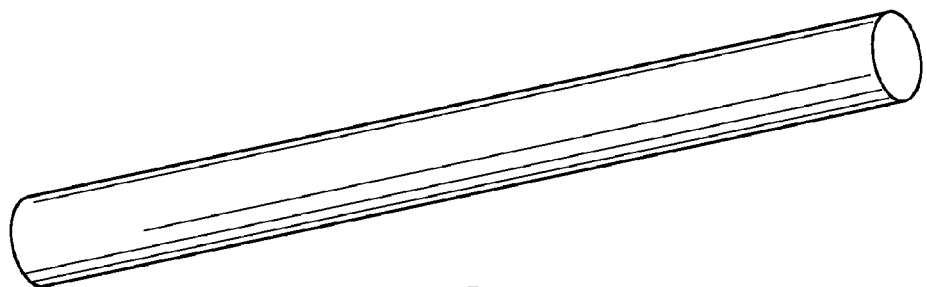
FIG. 11 is a perspective view of a first embodiment of a spinal rod that can be used in any of the embodiments of the growth rod distraction system or for any other spinal surgery for fusion or non-fusion technique in accordance with this invention.
Figure 12:
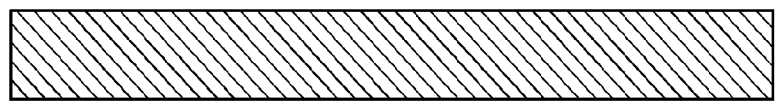
FIG. 12 is a sectional elevational view of the first embodiment of the spinal rod illustrated in FIG. 11.

FIGS. 11 and 12 illustrate a first embodiment of one of the rods 16, 25, and 36 that can be used in any of the above-described embodiments of the growth rod distraction system 10, 20, and 30, respectively. In this embodiment of the invention, the rod is formed completely from a solid piece of a flexible polymer material. For example, the rod may be formed from a PEEK (polyether ether ketone), carbon fiber PEEK, PEAK, or similar medical grade polymer material. The rod can be straight or curved as deemed necessary or desirable to correct the particular growth deformity. The rod can be of any desired size or cross sectional shape.

Figure 13:
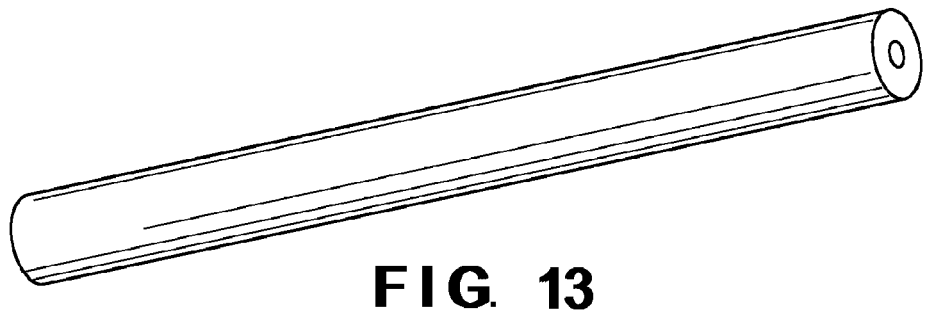
FIG. 13 is a perspective view of a second embodiment of a spinal rod that can be used in any of the embodiments of the growth rod distraction system or for any other spinal surgery for fusion or non-fusion technique in accordance with this invention.
Figure 14:
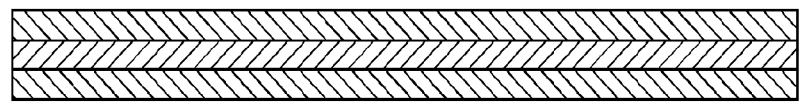
FIG. 14 is a sectional elevational view of the second embodiment of the spinal rod illustrated in FIG. 13.

FIGS. 13 and 14 illustrate a second embodiment of one of the rods 16, 25, and 36 that can be used in any of the above-described embodiments of the growth rod distraction system 10, 20, and 30, respectively. In this embodiment of the invention, the rod has a circumferential outer portion that is formed from a flexible polymer material (such as a PEEK, carbon fiber PEEK, PEAK, or similar medical grade polymer material) and an inner core that is formed from a metallic material (such as nitinol, titanium, stainless steel, or similar medical grade metallic material). The rod can be straight or curved as deemed necessary or desirable to correct the particular growth deformity. The rod can be of any desired size or cross sectional shape. The inner core may be formed from one piece of material or may be braided from a plurality of pieces of material.

FIGS. 15 and 16 illustrate a third embodiment of one of the rods 16, 25, and 36 that can be used in any of the above-described embodiments of the growth rod distraction system 10, 20, and 30, respectively. In this embodiment of the invention, the rod has a circumferential outer portion that is formed from a metallic material (such as nitinol, titanium, stainless steel, or similar medical grade metallic material) and an inner core that is formed from a flexible polymer material (such as a PEEK, carbon fiber PEEK, PEAK, or similar medical grade polymer material). The rod can be straight or curved as deemed necessary or desirable to correct the particular growth deformity. The rod can be of any desired size or cross sectional shape.

FIGS. 17 and 18 illustrate a fourth embodiment of one of the rods 16, 25, and 36 that can be used in any of the above-described embodiments of the growth rod distraction system 10, 20, and 30, respectively. In this embodiment of the invention, the rod has a circumferential outer portion that is formed from a metallic material (such as nitinol, titanium, stainless steel, or similar medical grade metallic material), an intermediate portion that is formed from a flexible polymer material (such as a PEEK, carbon fiber PEEK, PEAK, or similar medical grade polymer material), and an inner core that is formed from a metallic material (such as nitinol, titanium, stainless steel, or similar medical grade metallic material). The rod can be straight or curved as deemed necessary or desirable to correct the particular growth deformity. The rod can be of any desired size or cross sectional shape. The inner core may be formed from one piece of material or may be braided from a plurality of pieces of material.

Figure 19:
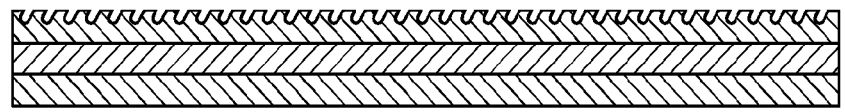
FIG. 19 is a sectional elevational view of a fifth embodiment of a spinal rod that can be used in any of the embodiments of the growth rod distraction system or for any other spinal surgery for fusion or non-fusion technique in accordance with this invention.

FIG. 19 illustrates a fifth embodiment of one of the rods 16, 25, and 36 that can be used in any of the above-described embodiments of the growth rod distraction system 10, 20, and 30, respectively. In this embodiment of the invention, the rod has a circumferential outer surface or portion having one or more serrations provided therein. The serrations can have any desired size, shape, orientation, and/or combinations thereof. The serrations allow the rod to be more flexible towards the serrated side, giving a surgeon more control of the angulation of the rod during installation.

Figure 20:
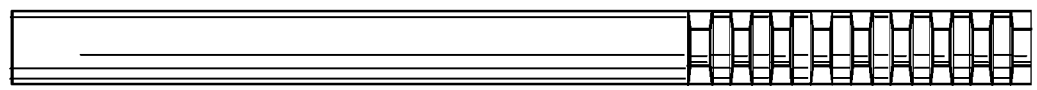
FIG. 20 is a sectional elevational view of a sixth embodiment of a spinal rod that can be used in any of the embodiments of the growth rod distraction system or for any other spinal surgery for fusion or non-fusion technique in accordance with this invention.

FIG. 20 is a sectional elevational view of a sixth embodiment of a rod that can be used in any of the embodiments of the growth rod distraction system in accordance with this invention. In this embodiment of the invention, the rod has a special internal rack region for use with the domino in the general manner described above. The rod and the internal rack region are both formed from a flexible polymer material (such as a PEEK, carbon fiber PEEK, PEAK, or similar medical grade polymer material).

Figure 21:
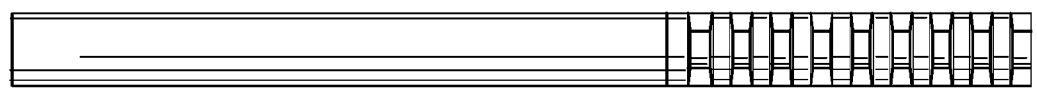
FIG. 21 is a sectional elevational view of a seventh embodiment of a spinal rod that can be used in any of the embodiments of the growth rod distraction system or for any other spinal surgery for fusion or non-fusion technique in accordance with this invention.

FIG. 21 is a sectional elevational view of a seventh embodiment of a rod that can be used in any of the embodiments of the growth rod distraction system in accordance with this invention. In this embodiment of the invention, the rod has a special internal rack region for use with the domino in the general manner described above. The rod is formed from a flexible polymer material (such as a PEEK, carbon fiber PEEK, PEAK, or similar medical grade polymer material), while the internal rack region is formed from a metallic material (such as nitinol or similar medical grade metallic material).

Figure 22:
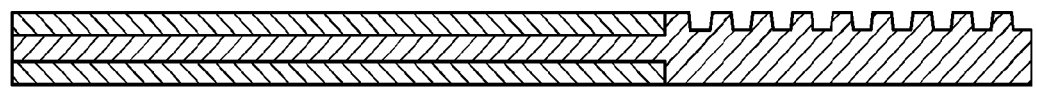
FIG. 22 is a sectional elevational view of an eighth embodiment of a spinal rod that can be used in any of the embodiments of the growth rod distraction system or for any other spinal surgery for fusion or non-fusion technique in accordance with this invention.

FIG. 22 is a sectional elevational view of an eighth embodiment of a rod that can be used in any of the embodiments of the growth rod distraction system in accordance with this invention. In this embodiment of the invention, the rod has an internal core and a special internal rack region for use with the domino in the general manner described above. The rod is formed from a flexible polymer material (such as a PEEK, carbon fiber PEEK, PEAK, or similar medical grade polymer material), while the internal core and the internal rack region are both formed from a metallic material (such as nitinol or similar medical grade metallic material).

Figure 23:
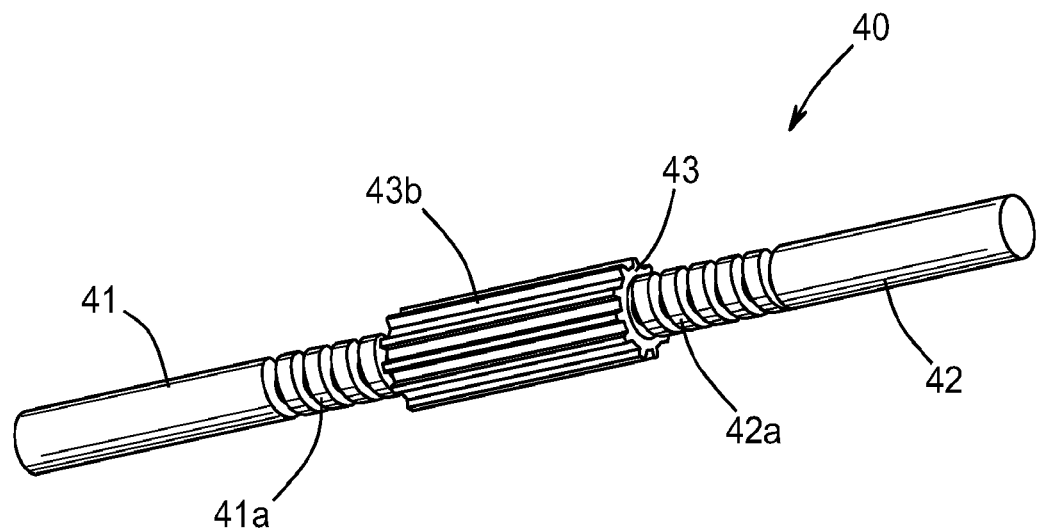
FIG. 23 is a perspective view of a portion of a fourth embodiment of a growth rod distraction system in accordance with this invention.
Figure 24:
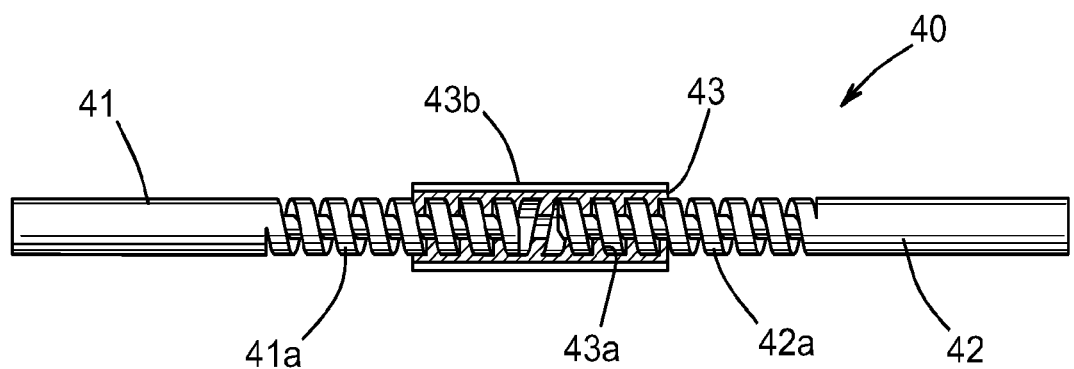
FIG. 24 is a side elevational view of the portion of the fourth embodiment of the growth rod distraction system illustrated in FIG. 23.

FIGS. 23 and 24 illustrate a portion of a fourth embodiment of a growth rod distraction system, indicated generally at 40, in accordance with this invention. In this embodiment of the invention, first and second growth rods 41 and 42 and a coupler gear 43 are supported within the domino (not shown). The ends of the first and second growth rods 41 and 42 have respective helical portions 41a and 42a that cooperate with an internal threaded surface 43a of the coupler gear 43. As a result, rotation of the coupler gear 43 relative to the domino causes axial movement of the first and second growth rods 41 and 42 in a manner that is similar to that described above. The coupler gear 43 is further provided with an external toothed surface 43b that cooperates with a bevel gear (not shown) or similar actuator for effecting rotation of the coupler gear 43 (and, therefore, axial movement of the first and second growth rods 41 and 42) relative to the domino.

The major mechanical failure associated with growth rods treatment is rod breakage and screw loosening. It has been found that the parameters of distraction force and distraction frequency can be manipulated to lower the rate of complication by reducing the stresses on rod and load on the screw. The use of electronics would render ease in achieving the required frequency of distraction. It could also be used to set an upper limit on the distraction forces that could results in failure stresses on rod and high loads at screw-bone interface.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A growth rod distraction system comprising:
a domino having a first bore provided therein, the first bore having an opened end and a closed end, and a second bore provided therein, the second bore having an opened end and a closed end;
a first growth rod disposed within the first bore for movement relative to the domino, the first growth rod having one end extending outward from the opened end of the first bore of the domino and an opposing end confined by the closed end of the first bore of the domino;
a second growth rod disposed within the second bore for movement relative to the domino, the second growth rod having one end extending outward from the opened end of the second bore of the domino and an opposing end confined by the closed end of the second bore of the domino; and
at least one gear disposed within the domino and cooperating with the first and second growth rods such that rotation of the gear causes axial movement of the first and second growth rods relative to the domino, wherein the axial movement of the first growth rod is opposite the axial movement of the second growth rod.

2. The growth rod distraction system defined in claim 1 wherein the gear is disposed within an opening provided in the domino, and wherein a head is provided that closes the opening and selectively prevents rotation of the gear.

3. The growth rod distraction system defined in claim 2 wherein the domino includes a post disposed within the opening, and wherein the gear is rotatably supported on the post.

4. The growth rod distraction system defined in claim 3 wherein the head has as aperture provided therein that receives the post therein.

5. The growth rod distraction system defined in claim 1 wherein the gear has one or more teeth provided thereon that cooperate with one or more recesses provided on the growth rod.

6. The growth rod distraction system defined in claim 1 wherein two gears are disposed within the domino and respective cooperate with the first and second growth rods such that rotation of the gears causes axial movement of the first and second growth rods relative to the domino.

7. The growth rod distraction system defined in claim 1 wherein the growth rod is formed from a polymer material.

8. The growth rod distraction system defined in claim 7 wherein the growth rod is formed from PEEK, carbon fiber PEEK, PEAK, or similar medical grade polymer material.

9. The growth rod distraction system defined in claim 1 wherein the growth rod is formed from a combination of polymer and metallic materials.

10. The growth rod distraction system defined in claim 9 wherein a first portion of the growth rod is formed from PEEK, carbon fiber PEEK, PEAK, or a similar medical grade polymer material, and wherein a second portion of the growth rod is formed from nitinol or a similar medical grade metallic material.

11. The growth rod distraction system defined in claim 9 wherein the growth rod has a circumferential outer portion that is formed from a flexible polymer material and an inner core that is formed from a metallic material.

12. The growth rod distraction system defined in claim 9 wherein the growth rod has a circumferential outer portion that is formed from a metallic material and an inner core that is formed from a flexible polymer material.

13. The growth rod distraction system defined in claim 9 wherein the growth rod has a circumferential outer portion that is formed from a metallic material, an intermediate portion that is formed from a flexible polymer material, and an inner core that is formed from a metallic material.

14. The growth rod distraction system defined in claim 1 wherein either of the first or second growth rods has a circumferential outer surface with at least a portion of the circumferential outer surface having one or more serrations provided therein.

15. The growth rod distraction system defined in claim 1 further including an actuator for selectively causing rotation of the gear.

16. The growth rod distraction system defined in claim 1 wherein the gear is a spur gear.

17. The growth rod distraction system defined in claim 1 wherein the gear is a coupler gear.

18. The growth rod distraction system defined in claim 1 wherein the domino is mounded with a electronic circuit and a motor to control the gear with a remote exterior to distract the rod.

\* \* \* \* \*